United States Patent [19]

Winston

[11] Patent Number: 5,443,835
[45] Date of Patent: Aug. 22, 1995

[54] BICARBONATE SALT PESTICIDE COMPOSITION CONTAINING A CLATHRATE SPREADER-STICKER INGREDIENT

[75] Inventor: Anthony E. Winston, East Brunswick, N.J.

[73] Assignee: Church & Dwight Co. Inc., Princeton, N.J.

[21] Appl. No.: 129,429

[22] Filed: Sep. 30, 1993

[51] Int. Cl.$^6$ .............................................. A01N 25/24
[52] U.S. Cl. .................................... 424/407; 424/405; 424/409; 424/715; 424/716; 424/717; 424/722
[58] Field of Search ............... 424/405, 407, 409, 489, 424/502

[56] References Cited

U.S. PATENT DOCUMENTS

| | | | |
|---|---|---|---|
| 2,906,744 | 9/1959 | Jancosek et al. | 260/96.5 |
| 2,916,414 | 12/1959 | Raecke et al. | 167/22 |
| 3,594,362 | 7/1971 | Szabo | 260/96.5 |
| 5,232,701 | 8/1993 | Ogawa et al. | 424/408 |

*Primary Examiner*—Thurman K. Page
*Assistant Examiner*—Neil Levy
*Attorney, Agent, or Firm*—Charles B. Barris

[57] ABSTRACT

This invention provides a dry blend pesticide composition which contains a fungicidal bicarbonate salt ingredient, and a spreader-sticker ingredient which is a crystalline clathrate complex of a urea constituent and a normally liquid spreader sticker constituent such as a nonionic surfactant. In a preferred embodiment all of the composition ingredients are water-soluble, and the composition is readily dispersible in an aqueous medium to form a sprayable pesticide solution.

14 Claims, No Drawings

BICARBONATE SALT PESTICIDE COMPOSITION CONTAINING A CLATHRATE SPREADER-STICKER INGREDIENT

BACKGROUND OF THE INVENTION

Fine chemical sales for agricultural purposes in the United States totalled about 13 billion dollars in 1990. The United States market for organic pesticide intermediates is about 986 million dollars per year, which include chemicals such as nitrites, amines, carboxylic acids, anilines, organophosphorus compounds, mercaptans, phenols, benzenes, alkane/alkenes, pyridines, alcohols and aldehydes.

Agricultural pesticide sales at the producer level in the United States in 1990 were about 5.5 billion dollars. Pesticide sales represent an important segment of the agrochemical industry in the United States and in other world markets, mainly for fungicide, herbicide and insecticide applications.

The control of phytopathogenic fungi is of great economic importance since fungal growth on plants or on parts of plants inhibits production of foliage, fruit or seed, and the overall quality of a cultivated crop.

There is also a serious worldwide problem of mold growth in food materials, such as grains, animal feeds, animal feed ingredients, and hay. This problem is most serious in tropical zones of both the eastern and western hemispheres, where sustained high humidities cause excessive moisture to be absorbed in such products.

Because of the vast economic ramifications of fungal propagation in agricultural and horticultural cultivations, a broad spectrum of fungicidal and fungistatic products have been developed for general and specific applications.

With respect to herbicide developments, weed control is essential in the cultivation of important agricultural crops such as corn, peanuts and cotton, and in the cultivation of many horticultural species. Also, the presence of weeds on non-cropped areas can be a fire hazard, or can result in undesirable drifting of sand or snow, or can cause discomfort to persons with allergies. Control of weeds is particularly beneficial when it permits the selective control of such plants without concurrent injury to desirable crops or vegetation.

Chemical herbicides are classified according to the type of activity they possess. A given compound may have more than one type of activity depending upon its mode of application and the rate at which it is applied. In addition, herbicides are usually classified as selective or non-selective pre-emergents or post-emergents.

Some herbicides are effective through contact, and others are taken up from the soil by root systems. Herbicide types include defoliants, desiccants, eradicants, systemics and selective herbicides, and related plant growth regulants.

With respect to insecticide developments, a wide variety of ornamental and agricultural plants are susceptible to infestation by insects and arachnids. The pests inflict damage by consuming foliage and roots, withdrawing juices from the plants, secreting toxins, and infecting with diseases.

Field crops which require protection from pests include such valuable crops as soybeans, corn, peanuts, cotton, alfalfa and tobacco. In addition, vegetables such as tomatoes, potatoes, sugar-beets, carrots, and the like, and nuts, ornamentals, apples, peaches, peas, citrus fruit and grape also require protection from the ravages of such pests.

A broad scope of insecticide compounds have been developed to combat insects which are harmful to agricultural and horticultural plants. Illustrative of insecticide compositions are those described in U.S. Pat. Nos. 3,217,037; 3,506,698; 3,576,834; 3,636,111; 3,755,364; 3,875,232; 4,028,413; 4,128,581; 4,415,743; 4,640,927; 4,804,653; 4,839,349; 5,010,068; 5,087,456; 5,087,456; 5,096,928; and references cited therein.

Of particular interest with respect to the present invention embodiments are pesticide compositions which contain one or more inorganic bicarbonate or carbonate compounds. It is known that bicarbonate and carbonate compounds exhibit biocidal properties for agricultural purposes.

Phytopathology, 48, 169 (1931) by R. H. Marloth describes studies involving the physiology of fungi. The reference reports studies which demonstrate that sodium and potassium bicarbonate and carbonate salts are toxic to fungi such as *Penicillum italicum* and *Penicillum digitalum*.

Japanese patent 56043207 describes a biocidal composition containing sodium bicarbonate and a polyglycerol fatty acid ester. The biocide controls *Penicillum digitatum* on oranges, *Sphaerotheca fuligenea* on cucumbers, *Piricularia oryzae* on rice, and mosaic virus on tomatoes.

Japanese patent 57062208 describes horticultural fungicides in which the addition of sodium bicarbonate to polyoxin or thiophanatemethyl increases the fungicidal activity of the organic biocide against *botrytis cinerea* on cucumbers.

Another significant factor involved in agricultural pesticide sales is the unit form and stability of packaged pesticide products. For purposes of economy and convenience, a pesticide product preferably is in the form of a free-flowing powder which is readily dispersible in water, and which does not agglomerate or deteriorate under ambient storage conditions. A free-flowing pesticide product is difficult to achieve when an ingredient such as a spreader-sticker organic compound is an oil or wax at ambient temperatures.

There remains a continuing need for the development of new and more effective forms of agrochemical compositions which possess preventive, curative and systemic biological activity for the protection of cultivated plants, with a minimum of phytotoxic side effects.

Accordingly, it is an object of this invention to provide an agricultural composition which is a combination of inorganic and organic compounds exhibiting pesticidal properties.

It is another object of this invention to provide a free-flowing pulverulent composition comprising a combination of ingredients which include a bicarbonate salt fungicidal ingredient and a crystalline spreader-sticker ingredient.

Other objects and advantages of the present invention shall become apparent from the accompanying description and examples.

DESCRIPTION OF THE INVENTION

One or more objects of the present invention are accomplished by the provision of a pesticide composition which is a dry blend formulation comprising (1) between about 45–80 weight percent of an ingredient selected from alkali metal and ammonium bicarbonates; (2) between about 0–35 weight percent of an ingredient selected from alkali metal and ammonium carbonates;

and (3) between about 0.5–50 weight percent of a spreader-sticker ingredient which is a crystalline clathrate of (a) a urea constituent complexed with (b) a spreader-sticker organic constituent which individually is non-crystalline at 20°–25° C.

A typical dry pulverulent composition is free-flowing and has an average particle size diameter in the range between about 1–600 microns. An invention pesticide composition can be in the form of a dusting powder which optionally can include a solid diluent such as bentonite, calcium carbonate, magnesia, gypsum, kieselguhr, diatomaceous earth, and the like. Plant foliage can be treated with a dusting powder, and ambient weather cycles and atmospheric conditions provide sufficient moisture to convert the applied dusting powder to an adherent coating on the plant foliage. A dusting powder preferably has an average particle size diameter between about 1–100 microns, and has a content of submicron particles.

A dry blend fungicide composition also can be diluted with water to form aqueous fungicidal solutions with controlled rheological properties. An aqueous fungicidal solution typically contains less than about 5 weight percent of active pesticidal ingredients, based on the solution weight. For most applications the content of bicarbonate ingredient is maintained at a concentration below about one weight percent, as a means of minimizing phytotoxic effects on treated plants which are sensitive to alkaline pH conditions.

In another embodiment this invention provides a method of controlling fungal disease in cultivated plants which comprises applying a present invention aqueous formulation to the plant foliage to prevent or eradicate fungal infections.

The term "water-soluble" as employed herein refers to an ingredient which has a solubility of at least 1.0 gram per 100 grams of water at 25° C.

The term "non-crystalline" as employed herein refers to a spreader-sticker organic constituent which normally is in the form of an oil or wax at a room temperature of 20°–25° C.

The bicarbonate salt ingredient of an invention pesticide composition is selected from compounds which include sodium bicarbonate, potassium bicarbonate and ammonium bicarbonate. In a further embodiment, a pesticide composition can include an additional compound selected from sodium carbonate, potassium carbonate, lithium carbonate and ammonium carbonate. A typical carbonate salt content is between about 1–20 weight percent.

Illustrative of inorganic salt ingredient combinations are mixtures such as sodium bicarbonate and potassium bicarbonate; sodium bicarbonate and ammonium bicarbonate; potassium bicarbonate and ammonium bicarbonate; sodium bicarbonate, potassium bicarbonate and ammonium bicarbonate; sodium bicarbonate and potassium carbonate; potassium bicarbonate and potassium carbonate; and the like.

Multiple inorganic salt compounds can be utilized in a broad range of molar quantities relative to each other. The molar quantity of a carbonate salt compound normally is determined by pH control considerations when aqueous formulations are prepared. The content of a carbonate salt compound can be varied to control the pH at a desired level in the range of 7.5–11. Aqueous pesticidal formulations of the present invention tend to have a higher biocidal activity at higher pH values.

The spreader-sticker ingredient of an invention pesticide is a crystalline clathrate which is a molecular complex of a urea type compound and a spreader-sticker organic constituent which in its normal free-state is non-crystalline at ambient temperatures.

Illustrative of urea type compounds are urea, methylurea, dimethylurea, tetramethylurea, monomethylolurea, dimethylolurea, hydroxyurea, thiourea, dimethylthiourea, and the like.

The spreader-sticker constituent which is occluded in the clathrate molecular complex typically is an organic oil or wax which has a chain length between about 6–30 carbon atoms, and additionally can contain other elements such as oxygen, sulfur or nitrogen atoms. The occluded long chain compound can be a nonionic, anionic, cationic or amphoteric surfactant; polyoxyalkylene glycol; triglyceride; a paraffinic type oil; and the like.

Oils which can be employed as the spreader-sticker occluded constituent in a crystalline clathrate include Orchex 796, Volck Oil #70, Sunoco Oil No. 7E, castor oil, corn oil, and similar nonphytotoxic spray oils of vegetable, animal or mineral origin commonly used in agricultural applications.

Suitable nonionic surfactants for molecular complexing with a urea compound are described in U.S. Pat. No. 2,814,611.

Illustrative of a crystalline clathrate is a combination of urea with a nonionic surfactant such as an ethoxylated $C_{12}$–$C_{15}$ alcohol containing an average of 7 moles of ethylene oxide. The clathrate can be prepared by heating a mixture of one part alcohol and 5 parts urea to 150° C. to form a melt, and then cooling the liquid mixture to yield a crystalline clathrate complex of the two compounds. A molar ratio of about 1:1 to 1:8 of urea to long chain compound can be employed. A higher urea content provides clathrates which are drier and more crystalline.

In an aqueous medium, the crystalline clathrate dissociates, and the urea compound and long chain compound function as separate molecules. The urea compound contributes nutrition when applied to cultivated plants, and the long chain compound exhibits spreader-sticker properties on plant foliage.

A present invention pesticide composition can contain between about 0.1–10 weight percent of an organic pesticide as an additional ingredient, such as a fungicide, insecticide, plant growth regulator, and the like, which exhibit an acceptable degree of phytotoxicity.

An optional fungicide ingredient can be selected from a wide variety of organic compounds or mixtures which are known and used in agriculture and horticulture applications, such as those listed in Agricultural Chemicals, Book IV, Fungicides, 1989 Revision (W. T. Thomson, Thomson Publications, Fresno, Calif. 93791).

The general categories of fungicidal-active compounds include anilides, dithiocarbamates, halogenated derivatives, heterocyclic nitrogen derivatives, organometallic derivatives, and the like.

Illustrative of fungicidal compounds are carbendazim, benomyl, thiophanate-methyl, thiabendazole, fuberidazole, dichlofluanid, cymoxanil, oxadixyl, metalaxyl, furalaxyl, benalaxyl, fenarimol, iprodione, procymidone, vinclozolin, penconazole, myclobutanil, pyrazophos, and the like.

An optional insecticide ingredient can be selected from a wide variety of organic chemical structures, such as those listed in Agricultural Chemicals, Book I, Insecticides, 1989 Revision (W. T. Thomson, Thomson Publications, Fresno, Calif. 93791).

The general categories of insecticidal-active organic compounds include chlorinated hydrocarbon derivatives, phosphorated derivatives, pyrethroids, acylureas, and the like.

The carbamates are similar in action to the organic phosphate insecticides. These insecticides usually are not magnified in the food chain, and are characterized by rapid breakdown.

The synthetic pyrethroids react well with synergists and exhibit relatively low mammalian toxicity. Generally they break down rapidly and leave little residue.

Illustrative of insecticidal compounds are chlorfluazuron, chlorpyrifos, chlorpyrifos methyl, bromophos, diazinon, malathion, trichlorfon, dimethoate, phorate, lindane, toxaphene, diflubenuron, methomyl, propoxur, carbaryl, cyhexatin, cypermethrin, permethrin, fenvalerate, dicofol, tetradifon, propargite, and the like.

An optional plant growth regulator ingredient can be selected from the types of organic chemical structures which are known to exhibit phytohormone activity, such as 3-indolealkanoic acids, deterpenoid acids, cytokinins, chloro-substituted phenoxyacetic acids, naphthaleneacetic acids, and the like.

Plant growth regulator compounds include abscisic acid, gibberellic acid, 3-indoleacetic acid, 2,4-dichlorophenoxyacetic acid, 2-naphthylacetic acid, 2,3,5-triiodobenzoic acid, phenyl indole-3-thiolobutyrate, kinetin, zeatin, 6-benzylaminopurine, and the like.

A present invention pesticide composition also can contain between about 0.01–5 weight percent of a water-soluble pseudoplastic thickener as an additional ingredient.

An optional thickener ingredient can be selected from water-soluble polymers which exhibit pseudoplastic properties in an aqueous medium such as gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyacrylamide, methyl vinyl ether/maleic anhydride copolymer, styrene/maleic anhydride copolymer, ethylene/maleic anhydride copolymer, the corresponding alkali metal salts of the maleic anhydride copolymers, alkali metal salts of poly(meth)acrylate, and the like.

Many of the water-soluble polymers are large volume commercial products. Sodium carboxymethyl cellulose (CMC) is available in powder or granular form having a particle size of 50–200 microns. CMC is available in a degree of substitution (DS) range of 0.38–1.4.

A present invention pesticide composition also can contain between about 0.2–10 weight percent of a particulate cationic, anionic or nonionic surfactant as an additional ingredient.

Surfactants suitable for incorporation in a present invention pesticide composition are listed in publications such as U.S. Pat. No. 3,541,213. One type of surfactant is an alkali metal or ammonium salt of a $C_8$–$C_{22}$ aliphatic-containing carboxylate, sulfonate, sulfate or phosphate.

Illustrative of other surfactant types are dioctyl sodium sulfosuccinate, cetyltrimethyl-ammonium bromide; sodium lauryl sulfate; sodium dodecylbenzenesulfonate; ammonium lignosulfonate; condensation products of ethylene oxide with fatty alcohols, amines or alkylphenols; partial esters of fatty acids and hexitol anhydrides; and the like.

A present invention pesticide composition also can contain between about 0.1–5 parts of particulate water-insoluble inert diluent per part of the other composition ingredients. Illustrative of inert diluents are bentonite, calcium carbonate, calcium silicate, magnesia, magnesium sulfate, gypsum, kieselguhr, diatomaceous earth, zinc stearate, and the like. The inert diluent can be selected to function additionally as a free-flow agent.

The ingredients in an invention pesticide composition can be selected to include nitrogen, phosphorus and potassium elements in a ratio that qualifies the composition to function as a fertilizer in addition to its function as a pesticide, when applied to cultivated crops. A typical ratio is 10-15-10. Besides nitrogen, phosphorus and potassium, an invention composition can contain trace elements, and other essential elements as exemplified by sulfur as contained in a compound such as sodium bisulfite or thiourea.

For purposes of this additional embodiment, the present invention provides a fungicide-fertilizer composition which is a dry blend formulation comprising (1) between about 45–80 weight percent of an ingredient selected from alkali metal and ammonium bicarbonates; (2) between about 0–35 weight percent of an ingredient selected from alkali metal and ammonium carbonates; (3) between about 0.5–50 weight percent of a spreader-sticker ingredient which is a crystalline clathrate of (a) a urea constituent complexed with (b) a spreader-sticker organic constituent which individually is non-crystalline at 20°–25° C.; and (4) between about 5–40 weight percent of an ingredient selected from phosphorus-containing fertilizer compounds; based on the composition weight; wherein the composition ingredients have a formulated ratio of nitrogen, phosphorus and potassium elements.

The dry blend fungicide-fertilizer composition can be dispersed in an aqueous medium, to provide a sprayable aqueous formulation which has a content of bicarbonate ingredient between about 0.1–5 weight percent, based on the formulation weight.

A pesticide composition of the present invention has a novel combination of properties for the practice of pest control in agricultural and horticultural applications.

The bicarbonate and carbonate ingredients exhibit fungicidal properties, and the efficiency of any additionally included organic pesticide ingredient usually is enhanced by the presence of the bicarbonate and carbonate ingredients. A lesser quantity of optional pesticide ingredient can be employed to achieve a desired degree of pest control.

A present invention fungicide composition can be formulated to exhibit no phytotoxicity, or to minimize the toxic effects of salt stress on plants by the bicarbonate ingredients.

A present invention pesticide composition provides particular advantage for the control of infectious phytopathogenic fungi which thrive under acidic soil conditions.

All of the invention pesticide composition ingredients are biocompatible when the composition is applied in an agricultural environment. The bicarbonate, carbonate and spreader-sticker ingredients are all harmless to animals and humans.

A significant feature of a present invention dry blend pesticide composition is the presence of a crystalline clathrate spreader-sticker ingredient when the pesticide composition is applied to plant foliage as a water-diluted solution. The clathrate molecular complex dissociates in the aqueous medium, and the urea constituent and the spreader-sticker organic constituent function as separate molecular species.

An applied aqueous solution forms an adherent coating of ingredients on plant foliage or fruit. A surfactant type ingredient aids in spreading and sticking the pesticide composition ingredients to the foliage or fruit to which it is applied. A hydrophilic polymer type ingredient increases the amount of aqueous pesticide composition which adheres to the plant surfaces because of its static high apparent viscosity. During a spraying procedure, the hydrophilic polymer ingredient contributes a low pseudoplastic viscosity to the spray solution, which facilitates the spraying action. After spraying, the applied coating resists drifting under wind conditions, and exhibits humectant properties in addition to enhanced pesticidal activity. Optionally, a hydrophilic polymer can be incorporated as an additional ingredient in an invention pesticide composition.

Another important advantage of a preferred invention pesticide composition derives from the water-solubility of the main ingredients. A coating of an invention pesticide composition on plant foliate or fruit can be removed readily by water-washing.

The unique free-flow properties of an invention dry blend pesticide formulation mainly are attributable to the incorporation of a urea compound and an oil or wax spreader-sticker organic compound in the form of a crystalline clathrate molecular complex. If urea is added to a dry blend pesticide formulation as an individual ingredient, the formulation gradually agglomerates and loses its free-flow state as the urea ingredient absorbs moisture under storage conditions.

If an oil or wax spreader-sticker organic compound is added to a blended pesticide formulation as an individual ingredient, a free-flowing dry blend composition is not obtained. An agglomeration of solids is formed, which is not readily dispersible in an aqueous medium.

The following examples are further illustrative of the present invention. The compounds and specific ingredients are presented as being typical, and various modifications can be derived in view of the foregoing disclosure within the scope of the invention.

EXAMPLE I

This Example illustrates the preparation of crystalline clathrates which are a molecular complex of urea and occluded spreader-sticker ingredient.

A.

A reaction flask is charged with 2 liters of ethanol and 450 grams of urea. The admixture is refluxed until a clear solution is obtained.

A 600 gram quantity of a 1-decanol is added to the flask contents, and the reaction medium is refluxed for 20 minutes. The reaction medium is cooled, and the crystalline clathrate product is recovered by filtration and dried.

B.

A 500 gram quantity of urea in a reaction flask is melted at 135° C. A 100 gram quantity of an ethoxylated $C_{10}$–$C_{12}$ alcohol (average of 7 moles of ethylene oxide) is heated to 100° C. in a separate reaction flask.

The ethoxylated alcohol is added to the melted urea with rapid stirring. The admixture is allowed to cool while maintaining the stirring action. A free-flowing crystalline powder is obtained.

EXAMPLE II

This Example illustrates the preparation and application of a fungicide composition in accordance with the present invention.

A free-flowing water-dispersible powder composition is prepared from the following weight percent ingredients:

| | |
|---|---|
| sodium bicarbonate | 48 |
| potassium carbonate | 30 |
| guar gum | 2 |
| dioctyl sodium sulfosuccinate | 3 |
| ultrafine silica | 2 |
| urea clathrate(1) | 15 |

(1) *Urea* (3:1) and occluded agricultural spray oil (Sunoco No. 7E)

The ingredients are blended and jet mill micronized to an average particle size of about 0 microns. If the clathrate constituents are added as separate compounds, a tacky agglomeration of particles is obtained.

Test plots are established in a field planting of cantaloupe, and the crop is inoculated with powdery mildew fungus (*Erysiphe cichoracearum*).

The test plots are sprayed with an aqueous dispersion of the powder composition. The bicarbonate content of the aqueous dispersion is 1.0 weight percent.

After a month, the treated plants in the test plots are healthy and growing rapidly. The untreated plants are damaged by powdery mildew, and are slow growing.

EXAMPLE III

This Example illustrates the preparation of a fungicide powder formulation for disease prevention in accordance with the present invention.

A blend of the following weight percent ingredients is prepared:

| | |
|---|---|
| sodium bicarbonate | 50 |
| potassium bicarbonate | 25 |
| sodium lauryl sulfate | 5 |
| xanthan gum | 5 |
| urea clathrate(1) | 15 |

(1) Dimethylolurea (3:1) and occluded dodecylphenol-condensate with 12 moles of ethylene oxide.

The dry free-flowing powder is diluted with water by the dispersion of 2 parts of the powder blend into 100 parts of water. The resulting solution is sprayed onto ornamental plant foliage where it forms an adherent coating on the foliage surfaces, and prevents fungal disease infection of the plants.

If the spreader-sticker constituent of the clathrate is added to the blend as a separate ingredient rather than as a clathrate constituent, the blend is not free-flowing and cakes on standing.

EXAMPLE IV

This example illustrates the preparation of a fungicide-fertilizer composition.

A blend of the following weight ratio of ingredients is prepared:

|  | Parts |
| --- | --- |
| melamine | 20 |
| urea clathrate[1] | 20 |
| KHCO$_3$ | 40 |
| Na$_2$CO$_3$ | 8 |
| K$_3$PO$_4$ | 10 |
| MgO | 2 |

[1]Urea (4:1) and occluded dodecanol containing an average of 7 moles of ethylene oxide.

Granules are prepared by tumbling the blend, spraying added water to form tacky solids, and then drying the granulated product.

The composition is used in granule form for application to soil, or the composition is dispersed in water for spray application to plant foliage.

EXAMPLE V

This Example illustrates the preparation of a herbicidal composition in the form of a water-soluble powder.

|  | Parts |
| --- | --- |
| NaHCO$_3$ | 60 |
| Na$_2$CO$_3$ | 20 |
| 2,4,5-trichlorophenoxy-acetic acid | 2 |
| Pluronic F-127 (BASF) | 1 |
| urea clathrate[1] | 10 |

[1]Thiourea (2:1) and occluded polypropylene glycol (M.W. 600).

The ingredients are blended to form a dry powder composition. The free-flowing powder is dissolved in water to provide an aqueous solution having a 200 ppm concentration of 2,4,5-trichlorophenoxyacetic acid which has utility as a herbicidal spray.

EXAMPLE VI

This Example illustrates the preparation of a free-flowing fungicide powder composition.

A blend of the following weight ratio of ingredients is prepared:

|  | Parts |
| --- | --- |
| potassium bicarbonate | 79 |
| urea clathrate[1] | 20 |
| magnesium oxide | 1 |

[1]Urea (5:1) and occluded nonylphenol containing an average of 7 moles of ethylene oxide.

The composition is used as a dusting powder, or the composition is dispersed in water for spray application to plant foliage.

What is claimed is:

1. A method of controlling fungal disease in cultivated plants which comprises applying a fungicidal aqueous formulation to the plant foliage by spraying to prevent or eradicate fungal infections; wherein the aqueous formulation is prepared by dispersing in an aqueous medium a dry blend formulation comprising (1) between about 45–80 weight percent of a fungicidal ingredient selected from alkali metal and ammonium bicarbonates; (2) between about 0–35 weight percent of a fungicidal ingredient selected from alkali metal and ammonium carbonates; and (3) between about 0.5–50 weight percent of a spreader-sticker ingredient which is a crystalline clathrate of (a) a urea constituent complexed with (b) a spreader-sticker organic constituent which individually in a free-state is non-crystalline at 20°–25° C.; and wherein the aqueous formulation has a content of bicarbonate ingredient between about 0.1–5 weight percent, based on the aqueous formulation weight, and has a pH between about 7.5–11.

2. An aqueous pesticide formulation which is prepared by dispersing in an aqueous medium a dry blend formulation comprising (1) between about 45–80 weight percent of a fungicidal ingredient selected from alkali metal and ammonium bicarbonates; (2) between about 0–35 weight percent of a fungicidal ingredient selected from alkali metal and ammonium carbonates; and (3) between about 0.5–50 weight percent of a spreader-sticker ingredient which is a crystalline clathrate of (a) a urea constituent complexed with (b) a spreader-sticker organic constituent which individually in a free-state is non-crystalline at 20°–25° C.; and wherein the aqueous formulation has a content of bicarbonate ingredient between about 0.1–5 weight percent, based on the aqueous formulation weight, and has a pH between about 7.5–11.

3. A pesticide formulation in accordance with claim 2 wherein the bicarbonate ingredient comprises at least two bicarbonate salt.

4. A pesticide formulation in accordance with claim 2 wherein the bicarbonate ingredient comprises sodium bicarbonate and potassium bicarbonate.

5. A pesticide formulation in accordance with claim 2 wherein the carbonate ingredient is selected from sodium carbonate and potassium carbonate.

6. A pesticide formulation in accordance with claim 2 wherein the crystalline clathrate ingredient contain urea, dimethylolurea or thiourea are the molecular complexing agent.

7. A pesticide formulation in accordance with claim 2 wherein the crystalline clalthrate ingredient contains a nonionic surfactant as the spreader-sticker organic constituent.

8. A pesticide formulation in accordance with claim 2 wherein the crystalline clathrate ingredient contains a constituent selected from anionic, cationic and amphoteric surfactants, either alone or in combination with a nonionic surfactant.

9. A pesticide formulation in accordance with claim 2 wherein the crystalline clathrate ingredient contains an agricultural spray oil as the spreader-sticker organic constituent.

10. A pesticide formulation in accordance with claim 2 wherein all of the ingredients are water-soluble.

11. A pesticide formulation in accordance with claim 2 which contains between about 0.01–10 weight percent of an organic fungicide, insecticide or plant growth regulator as an additional ingredient, based on the weight of dry blend ingredients.

12. A pesticide formulation in accordance with claim 2 which contains between about 0.01–5 weight percent of a water-soluble polymer thickener as an additional ingredient, based on the weight of dry blend ingredients.

13. A pesticide formulation in accordance with claim 2 which contains between about 0.2–10 weight percent a cationic, anionic, amphoretic or nonionic surfactant as an additional ingredient, based on the weight of dry blend ingredients.

14. An aqueous fungicide-fertilizer formulation which is prepared by dispersing in an aqueous medium a dry blend formulation comprising (1) between about 45–80 weight percent of an ingredient selected from alkali metal and ammonium bicarbonates; (2) between about 0–35 weight percent of an ingredient selected from alkali metal and ammonium carbonates; (3) between about 0.5–50 weight percent of a spreader-sticker ingredient which is a crystalline clathrate of (a) a urea constituent complexed with (b) a spreader-sticker organic constituent which individually is non-crystalline at 20°–25° C.; and (4) between about 5–40 weight percent of an ingredient selected from phosphorus-containing fertilizer compounds; wherein the aqueous formulation ingredients have a formulated fertilizer ratio of nitrogen, phosphorus and potassium elements, and wherein the aqueous formulation has a content of bicarbonate ingredient between about 0.1–5 weight percent, based on the aqueous formulation weight, and has a pH between about 7.5–11.

* * * * *